(12) United States Patent
Gagnon

(10) Patent No.: US 10,160,784 B2
(45) Date of Patent: *Dec. 25, 2018

(54) ANTIBODY PURIFICATION PROCESS

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 105 days.

This patent is subject to a terminal disclaimer.

(21) Appl. No.: 15/121,676

(22) PCT Filed: Feb. 27, 2014

(86) PCT No.: PCT/SG2014/000086
§ 371 (c)(1),
(2) Date: Aug. 25, 2016

(87) PCT Pub. No.: WO2015/130222
PCT Pub. Date: Sep. 3, 2015

(65) Prior Publication Data
US 2016/0362446 A1    Dec. 15, 2016

(51) Int. Cl.
*C07K 1/30* (2006.01)
*C07K 16/00* (2006.01)
*C07K 1/32* (2006.01)

(52) U.S. Cl.
CPC ............... *C07K 1/30* (2013.01); *C07K 1/32* (2013.01); *C07K 16/00* (2013.01)

(58) Field of Classification Search
None
See application file for complete search history.

(56) References Cited

U.S. PATENT DOCUMENTS

| 2012/0101262 A1 | 4/2012 | Arunakumari et al. |
| 2016/0272675 A1* | 9/2016 | Jungbauer .............. C07K 16/00 |

FOREIGN PATENT DOCUMENTS

| JP | S63-283596 | 11/1988 |
| WO | WO 2010/15163 | 12/2010 |
| WO | WO2013/180647 A1 | 12/2013 |
| WO | WO 2013/180650 A1 | 12/2013 |
| WO | WO2013/180655 A1 | 12/2013 |
| WO | WO 2014/123484 A1 | 8/2014 |
| WO | WO 2014/123485 A1 | 8/2014 |
| WO | WO2014/196926 A1 | 12/2014 |
| WO | WO 2015/126330 A2 | 8/2015 |

OTHER PUBLICATIONS

Written Opinion dated Mar. 21, 2017 for SG Patent Application No. 11201607985.
International Search Report and Written Opinion dated Jun. 4, 2014 for PCT/SG2014/000086.
International Preliminary Report on Patentability dated Sep. 9, 2016 for PCT/SG/2014/000086.
Gagnon, "Purification Tools for Monoclonal Antibodies", Validated Biosystems, 1996, pp. 1-269.
Extended European SearchReport dated Dec. 9, 2017, for related European Patent App. No. 14883697.6.
Gan et al., "Characterization and removal of aggregates formed by nonspecific interaction of IgM monoclonal antibodies with chromatin catabolites during cell culture production", Journal of Chromatography A 1291, (2013), pp. 33-40.
Chanutin, et al., "The precipitation of Plasma Proteins by Short-Chain Fatty Acids"; Arch. Biochem. Biophys. 89 (1960) pp. 218-220.
Brodsky et al, "Caprylic acid precipitation method for impurity reduction: an alternative to conventional chromatography for monoclonal antibody purification", Biotechnol. Bioeng. 109 (2012), pp. 2589-2598.
Vagenende et al., "Amide-mediated hydrogen bonding at organic crystal/water interfaces enables selective endotoxin binding with picomolar affinity", AACS. Appl. Mater. Interfaces, 22 (2013) pp. 4472-4478.
Morals et al, "A model mechanism for protein precipitation by capryllc acid: Application to plasma purification", vol. 59, No. 1, 2012, pp. 50-54.
Vagenende et al, "Allantoin as a solid phase adsorbent for removing endotoxins" Journal of Chromatography A, 1310 (2013), pp. 15-20.
Kuczewski et al., "A single-use purification process for the production of a monoclonal antibody produced in a PER.C6 human cell line", Biotechnology Journal, 2011, 6, pp. 56-65.
Lain et al., "PEG precipitation: a powerful tool for monoclonal antibody purification", BioPharm, 2010, pp. 1-8.
McKinney et al., "A simple non-chromatographic procedure to purify immunoglobulins from serum and ascites fluid", Journal of Immunological Methods, 96, (1987), pp. 271-278.
English translation of Japanese Office Action dated Dec. 12, 2017, for related Japanese Patent Application No. 2016-553658.
Horio, Takeichi, Table 2.2 Structure and Properties of Surfactants, Fundamental Experimental Methods for Proteins and Enzymes, 2000, Revision 2nd edition, pp. 66-67.

* cited by examiner

Primary Examiner — Daniel E Kolker
Assistant Examiner — James L Rogers
(74) Attorney, Agent, or Firm — Pillsbury Winthrop Shaw Pittman, LLP

(57) ABSTRACT

A method of purifying a target antibody includes contacting a cell culture harvest or a protein preparation including at least one target antibody with at least one fatty acid having 7 to 10 carbon atoms to form a mixture, contacting this mixture with allantoin, and then separating solid materials to provide a solution comprising the target antibody. Solid materials can be removed by filtration, sedimentation or centrifugation, and the fatty acids can be enanthic, caprylic, pelargonic, nonenoic or capric acid. The invention is also directed to kits used to facilitate this method of antibody purification.

20 Claims, No Drawings

ANTIBODY PURIFICATION PROCESS

RELATED APPLICATIONS

This application is a U.S. National Stage of International Patent Application No. PCT/SG2014/000086, filed Feb. 27, 2014, entitled ANTIBODY PURIFICATION PROCESS, and naming inventor Peter Stanley Gagnon, which published as International Patent Publication No. WO/2015/130222 on Sep. 3, 2015. The entire content of the foregoing application is incorporated herein by reference, including all text, tables and drawings.

BACKGROUND

Embodiments disclosed herein relate to methods for purifying proteins, including antibodies, such as IgG and IgM antibodies.

Purification of proteins typically begins with a clarification step in which cells and debris are removed so that the remaining supernatant can be processed by methods that would otherwise be hampered by their presence. Their removal commonly involves physical methods such as centrifugation and filtration. This step sometimes involves the use of filtration materials with anion exchange capabilities, or the addition of anion exchange particles or soluble polymers directly to the antibody-containing harvest (Gagnon, P., Purification Tools for Monoclonal Antibodies, Validated Biosystems, Tucson, 1996; Kuczewski, M,. et al, Biopharm Int. 23(3) (2010) 20-25; Kuczewski, M., et al, Biotechnol. J., 6 (2011) 56-65.

Secondary treatment of physically clarified cell culture harvests with allantoin, soluble organic cations, and mixed particles has been described (Gan, H. et al J. Chromatogr. A, 1291 (2013) 33-40). This approach particularly reduced the content of chromatin expelled by dead cells and the levels of aggregates associated with chromatin, but three chromatography steps were subsequently needed to achieve the desired purity. Allantoin is an FDA-approved anti-inflammatory agent used widely in over-the-counter healthcare products. It is known to remove endotoxin from protein solutions, including from solutions of IgG, apparently through hydrogen bonding (Vagenende et al, ACS. Appl. Mater. Interfaces, 22 (2013) 4472-4478; Vagenende et al, J. Chromatogr. A 1310 (2013) 15-20).

Partial purification of IgG antibodies by contaminant co-precipitation with caprylic acid (octanoic acid) has been disclosed (Chantuin, A., et al, Arch. Biochem. Biophys. 89 (1960) 218-220; McKinney, M. et al, J. Immunol. Met., 96 (1987) 271-278). The fatty acid binds to all proteins but tends particularly to precipitate acidic non-IgG contaminants (Gagnon supra; Morais, V., et al, Biotechnol. Appl. Biochem., 59 (2012) 50-54). The mechanism and process development guidelines for application to cell culture harvests have been indicated (Gagnon supra), including basic variables such caprylic acid concentration, pH, salt concentration, temperature, and the need for a subsequent chromatography step to remove residual caprylic acid from the soluble IgG preparation. The technique is most often described to prepare crude samples for subsequent purification by other means (Gagnon supra; Y. Yigsaw et al, 2008, Improving upstream feed stock to downstream operations, Recovery of Biologics Conference XIII, Quebec; Arunakumari, A. et al, US Patent Application 20120101262 A1), but has also been applied as a polishing step following antibody capture by protein A affinity chromatography (Y. Brodsky et al Biotechnol. Bioeng. 109 (2012) 2589-2598).

SUMMARY

In some aspects, embodiments disclosed herein relate to methods of purifying a target protein comprising contacting a cell culture harvest with at least one fatty acid having 7 to 10 carbon atoms, and allantoin in a supersaturating concentration to form a mixture, and separating solid materials to provide a solution comprising the target protein with a reduced load of contaminants. The processed liquid may optionally, be further passed through a device with an internal contact surface contact that comprises positive charges before being processed by other purification methods, if desired.

In some aspects, embodiments disclosed herein relate to methods for purifying an antibody comprising contacting a cell culture harvest with at least one fatty acid having 7 to 10 carbon atoms to form a mixture, contacting the mixture with allantoin, and contacting the mixture with a nonionic or cationic surfactant, then removing solid materials after to provide a solution comprising the antibody.

DETAILED DESCRIPTION

It has been discovered that a combination of materials that are chemically antagonistic to one another has the unexpected effect of providing target proteins, including antibodies, at a higher level of purity and a lower level of turbidity than purification methods relying on any one of the materials individually. Combinations of antagonistic materials would normally be expected to cancel each other's individual effects and result in inferior protein purification, inferior protein recovery, or both. Instead, the present embodiments provide defined windows within which the materials work synergistically to achieve levels of protein purity and recovery that are substantially beyond the ability of any of the individual components to provide.

These observations are particularly applicable to antibodies, such as IgG and IgM antibodies. In addition, experimental results indicate that reactivity curves for each of the components in the combination is distinct from their reactivity curves when used individually. This highlights that the utility of the embodiments disclosed herein could not have been predicted by the known properties or applications of the individual components. The components to, be combined particularly include saturated fatty acids containing 7 or 8 or 9 or 10 carbon atoms, or unsaturated fatty acids containing 6 or 7 or 8 or 9 carbon atoms and 1 double bond; and soluble and/or solid materials bearing a positive charge. They may further include allantoin. In the methods disclosed herein, the materials are combined in a liquid preparation containing a target protein, such as a species of antibody, then after a suitable period of incubation, solids are removed to provide a solution comprising the antibody.

Experimental data indicate the mutually antagonistic interactions among the components employed in methods disclosed herein. In one example of mutual antagonism, crystalline allantoin has been shown experimentally to bind more than 99% of the fatty acids in cell culture harvest, indicating a high likelihood that it acts on added fatty acids in a similar manner. This should be expected to reduce the effectiveness of fatty acids added to an antibody-containing cell culture harvest for the purpose of precipitating non-antibody contaminants. To the contrary, this aspect of the methods disclosed herein contributes to effective use of fatty acids at concentrations less than half the levels reported as optimum in the scientific literature. Without being bound by theory, it may be that fatty acids complexed to undissolved allantoin through hydrogen bonding conserve their native charge, hydrophobicity, and ability to bind contaminants, while the physical density of the undissolved allantoin enhances their removal by sedimentation. In another example of mutual antagonism, the addition of very low concentrations of nonionic surfactants that weaken hydrophobic interactions and would thereby be expected to interfere with the ability of fatty acids to achieve their effects, surprisingly improve the effectiveness of removing free light chain contaminants, while larger amounts compromise removal of acidic non-antibody proteins. In another, more surprising example, low levels of cationic surfactants, which should interfere with both the charge and hydrophobic effects of fatty acids, roughly double the ability of the combination to remove acidic non-antibody proteins, while higher concentrations have the opposite effect. These examples highlight that when normally antagonistic components are combined in properly balanced proportions, they create windows within which it is possible to remove contaminants that are not removed effectively in the absence of such antagonists.

It has been further discovered that the inclusion of allantoin particularly enhances the ability of fatty acid precipitation to remove particulates. Without being bound by theory, the effects of allantoin are believed to be mediated through hydrogen bonding, by which large molecular assemblages, including ultra-small particles, including viruses, are bound to the larger allantoin crystals. Due to its relatively high density of 1.45 g per cubic cm, allantoin crystals promote rapid gravimetric sedimentation of associated materials, and enhance their sedimentation by centrifugation. Allantoin crystals also alter the physical constitution of fatty acid-contaminant precipitates from a typically gluey sludge, to a more cake-like consistency that facilitates the passage of liquid and improves filtration efficiency. A portion of the allantoin added to an aqueous solution dissolves, up to a maximum of about 36 mM, and is believed to weaken the interaction of proteins with fatty acids. Dissolved allantoin is understood to remain in the antibody-containing solution after removal of solids. While these features are welcome, they represent a paradox since experimental data indicate that allantoin binds 99.7% of fatty acids from cell culture harvests. As this implies, the proportion of allantoin is ideally carefully controlled. The appropriate proportion for a give application is determined by simple experimentation, generally starting with 1-2% (w/v).

It has also been discovered that methods disclosed herein unexpectedly allow saturated fatty acids with 7 or 9 or 10 carbon atoms to be substituted for caprylic acid. Enanthic (heptanoic) acid contains 7 carbons. Pelargonic (nonanoic) acid contains 9 carbons. Capric (decanoic) acid contains 10 carbons. Even more surprisingly, unsaturated fatty acids with 6 or 7 or 8 or 9 carbon atoms and 1 double bond are effective. Despite species other than octanoic acid being neglected in the scientific literature for antibody purification, experimental data indicate that more hydrophobic fatty acids more effectively remove antibody aggregates and fragments than caprylic acid, though at higher risk of reducing antibody recovery.

In one exemplary embodiment that illustrates the integration of numerous aspects of the methods disclosed herein, allantoin is added to an antibody-containing cell culture harvest in an amount to produce a final concentration of 1% (w/v), followed by addition of nonanoic acid in an amount to produce a final concentration of 0.3% (v:v). The mixture is incubated for 2 hours, during which a precipitate is formed by the interaction of nonanoic acid with contaminants, and which is interspersed with undissolved allantoin crystals. Mixing is terminated and the solids, consisting of nonanoic acid-allantoin-contaminant precipitates, residual nonanoic acid, and undissolved allantoin, are removed by any expedient method. In a related embodiment, the substantially solids-free antibody-containing liquid is further processed by passage through an electropositive depth filter, or other device in which the sample contacts an electropositive or other functionalized surface, and which may provide the additional benefit of scavenging residual fatty acid or other soluble non-antibody species from the sample.

In another exemplary embodiment that illustrates integration of various aspects of the methods disclosed herein, allantoin is added to cell culture harvest in an amount to produce a final concentration of 2% (w/v) followed by addition of capric acid in an amount to produce a final concentration of 0.2% (v:v). The mixture is incubated for 2 hours, during which a precipitate is formed by the interaction of capric acid with contaminants, and which is interspersed with undissolved allantoin crystals. The mixture is then contacted with a device comprising at least one functionalized solid that retains, capric acid-contaminant precipitates interspersed with undissolved allantoin but permits the passage of liquid.

In another exemplary embodiment that illustrates integration of various aspects of the methods disclosed herein, allantoin is added to cell culture harvest in an amount to produce a final concentration of 1% (w/v) followed by addition of nonenoic acid in an amount to produce a final concentration of 0.5% (v:v). The mixture is incubated for 2 hours, during which time a precipitate is formed by the interaction of nonenoic acid with contaminants, and which is interspersed with undissolved allantoin crystals. Nonenoic acid-allantoin-contaminant precipitates interspersed with undissolved allantoin are removed by any expedient method.

In some embodiments, about 0.2% capric acid may be replaced with pelargonic acid at a concentration, of about 0.3%, or caprylic acid at a concentration of about 0.4% or enanthic acid at a concentration of about 0.6%. This reveals the dependency of contaminant removal and antibody recovery on the concentration and hydrophobicity of the fatty acid. It has been observed that the more hydrophobic the fatty acid, the lower the concentration needed to achieve a good result, and also the lower the concentration to compromise IgG antibody recovery. It will be understood that the absolute and relative concentration may vary from one antibody to another and that the above concentrations of the specific fatty acids may therefore vary, but such values are provided to inform the skilled artisan of a convenient starting point when assessing purification in a new antibody system.

In some embodiments, about 0.2% caprylic acid may support more effective aggregate removal than at higher concentrations. However, at about 0.4%, more effective removal of free antibody light chain, light-chain dimers, and other fragmentary forms, as well as other contaminants may be achieved. Thus, one skilled in the art will recognize the value of optimizing the concentration of a given fatty acid by consideration of its effects in the context of potential follow-on fractionation methods. If methods disclosed herein are to be followed by a method that is particularly suitable for removal of aggregates, it may be beneficial to optimize the fatty acid concentration to remove antibody fragments. If methods disclosed herein are to be followed by a method particularly suitable for removing fragments, it may be beneficial to optimize the fatty acid concentration to remove aggregates.

In some embodiments, allantoin may be added after the fatty acid. In another related embodiment, allantoin is not added until after the precipitate has formed. In another embodiment allantoin is not added until after the precipitate has been removed. In some embodiments, allantoin is omitted.

In some embodiments, a non-ionic surfactant or a zwitterionic surfactant may be added to the mixture at a concentration below its critical micelle concentration. Experimental data indicate that this improves removal of antibody fragments, while surfactant concentrations above the critical micelle concentration suppress the removal of antibody fragments, though with the offsetting benefit of increasing antibody recovery. In some embodiments, a substantially higher concentration of a non-ionic or zwitterionic surfactant may substantially compromise reduction of acidic host cell proteins.

In some embodiments, a low concentration of a cationic surfactant may substantially enhance the removal of host proteins and DNA. In some such embodiments, the cationic surfactant is hexadecyltrimethylammonium bromide, also known as cetyltrimethylammonium bromide (CTAB); or dodecyltrimethylammonium bromide; or decyltrimethylammonium bromide; or myristyltrimethylammonium bromide; or trimethyloctadecylammonium bromide, or variations with a different positively charged moiety, such as a primary, secondary, or tertiary amino group, or variations with more or fewer carbon atoms. In some such embodiments, 0.01% CTAB may double the amount of host protein removed, whereas 0.05% CTAB may reduce removal efficiency by a factor of 5.

In some embodiments, one or more chemically functionalized solids may be replaced by or combined with soluble entities chemically functionalized with the same or similar moieties.

In some embodiments, solids may be separated from the antibody-containing solution by any expedient means, including filtration or sedimentation, including one or more treatments from the groups comprising microfiltration, depth filtration, and centrifugation, where depth filtration may be performed with filtration media that are substantially inert or with filtration media that have been chemically functionalized, or combined with materials that are chemically functionalized.

In some embodiments, allantoin may be added at a weight to volume concentration of about 0.6 to about 30%, or about 1 to about 30%, or about 1 to about 10%, or about 1 to about 2%. In some embodiments, allantoin may be omitted. In some embodiments, allantoin may be present in a non-zero amount up to about 0.6%. While the presence of allantoin may be desired at a concentration sufficient that a portion of the added allantoin does not dissolve, such as 1%, methods may produce adequate results in the absence of allantoin, or in the presence of allantoin at a concentration where substantially all of the allantoin is soluble. Experimental data indicate that larger proportions of allantoin, such as 2%, 3%, 4%, 5%, 10% or higher support more effective reduction of aggregates, but also reduce antibody recovery, modestly but measurably. Experimental data also reveal that allantoin can independently reduce levels of virus and endotoxin, by 3 logs or more, and generally produce supernatants that are remarkably clear (2.0 NTU), all of which document that allantoin makes a favorable contribution to methods disclosed herein, when employed. Without being bound to any particular theory, it appears that allantoin's mechanism of action with large biological species and assemblages primarily involves hydrogen bonding, which may explain in part why its effectiveness is little affected by substantial variations in pH or conductivity. This could also explain why fatty acids bound to allantoin retain their interactivity with contaminants.

In some embodiments, the fatty acid may include one or more species with a general structural formula of $CH_3(CH_2)_n COOH$, where n is an integer from 4 to 12, inclusive. In some embodiments, n is an integer from 5 to 8. In some such embodiments, the fatty acid may be enanthic acid (heptanoic acid). In some such embodiments, the fatty acid may be caprylic acid (octanoic acid). In some such embodiments, the fatty acid may be pelargonic (nonanoic acid). In some such embodiments, the fatty acid may be capric acid (decanoic acid). In some embodiments, more than one species of fatty acid may be employed. In some embodiments, the fatty acid may be added in the form of a salt, such as a sodium salt, for example sodium caprylate. In some embodiments, the fatty portion of the fatty acid may consist of a linear "straight" chain of carbon atoms. In some embodiments, the fatty portion of the fatty acid may consist of a branched chain, such as 2-ethylhexanoic acid, which contains a 2-carbon chain at the number 2 position of the primary 6-carbon chain, producing a total of 8 carbon atoms. In some embodiments the fatty acid may be present at a concentration 0.05 to 5%, or 0.1 to 2%, or 0.2 to 0.5%, or an intermediate value.

In some embodiments, the fatty acid may include a double bond. In some such embodiments the double bond may be at any position in the carbon chain. In some such embodiments, the fatty acid chain may contain 6 or 7 or 8 or 9 carbon atoms. In one such embodiment, the fatty acid is nonenoic acid with a terminal double bond. In some embodiments, the fatty acid may be added in the form of a salt. In some embodiments the fatty acid may be present at a concentration 0.05 to 5%, or 0.1 to 2%, or 0.2 to 0.5%, or an intermediate value. In some such embodiments, 0.4% to 0.6% 8-nonenoic acid provides better results than 0.4% caprylic acid.

In some embodiments, employing more than one species of fatty acid, the species may be selected to encompass a range of hydrophobicities, for example the combination of heptanoic and decanoic acid, or the combination of caprylic and nonanoic acid, or other combinations, potentially including fatty acids of greater or lesser hydrophobcity. In some such embodiments, the proportions of the respective fatty acids may be 10:1, 5:1, 2:1, 1:1, 1:2, 1:5, 1:10, or any intermediate range in between, or other ratios outside of these. In some such combinations the total amount of fatty acid species added to a working solution may be in the range of a non-zero amount up to 0.01%, 0.01 to 0.1%, 0.1 to 1%, 1 to 5%, 0.2 to 0.4%, or an intermediate range or value.

In some embodiments employing more than one species of fatty acid, the total number of species may include 3, or 4, or more, in any proportion; and in any total amount shown by experimental results to provide utility.

In some embodiments, the fatty acid is left to incubate in the antibody preparation for 5 to 360 minutes, or 15 to 240 minutes, or 60 to 120 minutes, or 30 to 60 minutes, or for an intermediate interval, before exposing the mixture to the one or more functionalized solids.

In some embodiments, the temperature at which the fatty acid is incubated may be influenced by the largest species of fatty acid present, since carbon chain length directly influences fatty acid solubility, where the shorter the chain length, the higher the solubility, and where the longer the chain length, the greater the diminution of solubility with decreasing temperature. Thus in all cases, an initial temperature of about 37° C. will solvate a higher concentration of fatty acid than lower temperatures. This favors direct addition of the fatty acid to the harvest immediately following termination of the cell culture. Incubation may subsequently continue at 37° C., still in the bioreactor. It will be apparent that the more hydrophobic the fatty acid, the more sensitive its solubility to temperature, and therefore the more sensitive its functionality to temperature. In some embodiments, higher temperatures may allow the use of fatty acids up to $C_{12}$, $C_{13}$, $C_{14}$, $C_{15}$, or even higher. In some embodiments employing lower temperatures, for example where processing is conducted at about 2 to about 8° C., the use of shorter chain fatty acids may be favored, such as C8, C7, C6, or even lower.

In one embodiment, methods disclosed herein may need no pH adjustment. Addition of the fatty acid may reduce the pH of the harvest to a sufficiently low level, and subsequent scavenging of excess fatty acid by the one or more solids may substantially restore the pH to the original value. In one embodiment, the harvest may be titrated to a particular pH value before addition of the fatty acid, which may add robustness to the method, but which may necessitate that the pH be adjusted again after the method has been performed, potentially for the purpose of preparing the sample to be fractionated to a higher degree of purity by a subsequent method. In one embodiment, the initial pH may be adjusted to a value in the range of 4 to 6, or 4.5 to 5.5, or 4.75 to 5.25, or 5.1 to 5.3, or an intermediate value such as 5.2, or another intermediate value. It will be understood by the person of skill in the art that the optimum pH may vary from one species of antibody to another; and according to the composition of medium in which the antibody is resident. It will be equally understood that the pH employed to achieve optimal results may be more moderate than required with fatty acid precipitation alone due to the contributions of the additional elements of the methods disclosed herein. This is a noteworthy consideration because exposure to the low pH values associated with traditional use of fatty acid precipitation are in a range that may have lasting adverse effects on the antibody. This highlights another unexpected benefit of the disclosed methods.

In one embodiment, methods disclosed herein need not adjust conductivity through either a reduction or increase of salt concentration, such as with water or with NaCl or other salt. Salt concentration is known however to affect antibody recovery and purity, and variations may be explored without departing from the essential features of the method. Experimental evidence indicates that antibody solubility becomes compromised in conditions of low conductivity and low pH, independently from the presence of fatty acids or other additives. Poor antibody solubility translates to an elevated probability, of significant antibody loss in conjunction with fatty acid precipitations. This means that reduction of pH may limit the degree to which conductivity can be reduced, and may suggest that conductivity be increased to avoid excessive loss of antibody. Remarkably, the effectiveness of the methods disclosed herein are not substantially decreased by increased conductivity up to 20 mS/cm. This is remarkable because charge interactions are believed to control a major proportion of the selectivity of the system, and 20 mS/cm is sufficient to suspend many such interactions, and substantially weaken all such interactions. It is to be understood however, that results may vary depending on the exact antibody being purified, and there may be value in conducting experiments at lower conductivity values. Reducing conductivity would appear to increase interference of the cationic solids with the interaction of a fatty acid and contaminating proteins, but could unexpectedly produce an improved overall result by increasing the ability of the cationic solids to bind soluble contaminants.

In one or more of the previous embodiments, solid materials present after contacting a cell culture harvest with the at least one fatty acid or at the separating step, are removed by sedimentation or sedimentation following centrifugation.

In one or more of the previous embodiments, solid materials present after contacting a cell culture harvest with the at least one fatty acid or at the separating step, are removed by filtration. In some such embodiments, filtration comprises membrane filtration or depth filtration. In some such embodiments, the membrane filtration or depth filtration comprises a filter membrane that is functionalized. In some such embodiments, at least one functional group is electropositive. In some such embodiments at least one functional group binds metal ions.

In one or more of the previous embodiments, the first contacting step is preceded by partial purification of the IgG antibody.

In one or more of the previous embodiments, the cell culture harvest contains cells. In one or more of the previous embodiments, the cell culture harvest does not contain cells.

In one or more of the previous embodiments, the at least one fatty acid comprises a general structural formula of $CH_3(CH_2)_nCOOH$. In some such embodiments, the at least one fatty acid comprises enanthic (heptanoic) acid, or caprylic (octanoic) acid, or pelargonic acid, or capric (decanoic) acid. In some related embodiments, the fatty acid may contain a single double bond at any position of the fatty acid chain. In some such embodiments, the fatty acid containing the double bond is nonenoic acid. In some such embodiments, the fatty acid is 8-nonenoic acid. In some embodiments, the primary carbon chain may be unbranched; in others branched.

In one or more of the previous embodiments, the at least one fatty acid is present at a concentration in a range selected from the group consisting of: (a) from about 0.05 to about 5%, (b) from about 0.1 to about 1.0%, (c) from about 0.2 to about 0.4%, and (d) from about 0.1 to about 0.2%.

In one or more of the previous embodiments, a cationic surfactant may be present at a concentration of: (a) from about 0.001 to 0.1%, (b) from about 0.005 to 0.05%, (c) from about 0.0125 to 0.025%. In one or more of the previous embodiments, a cationic surfactant may be cetyltrimethylammonium bromide.

In one or more of the previous embodiments, a hydrophobic cation component may be aromatic in nature, such as benzalkonium chloride, or chlorhexidine, or alexidine. In one such embodiment, the concentration of chlorhexidine may be in the range of: (a) from about 0.001% to 0.01%, (b) from about 0.005 to 0.05%, (c) from about 0.0075 to about 0.0125%.

In some embodiments, there are provided methods for purifying an IgG antibody comprising contacting a cell culture harvest with at least one fatty acid having 8 to 10 carbon atoms to form a mixture, contacting the mixture with allantoin; and separating solid materials after contacting the mixture with allantoin to provide a solution comprising the IgG antibody.

In one or more of the previous embodiments, allantoin is present at a concentration in a range selected from the group consisting of: (a) from about 0.6 to about 30%, (b) from about 1 to about 10%, and (c) from about 1 to about 2%. In one or more of the previous embodiments, allantoin is in a range from a non-zero amount up to about 0.6%.

In some embodiments, the method is applied to monoclonal or polyclonal IgG antibodies of natural origin, such as serum or plasma. In some embodiments, the method is applied to fragmentary immunoglobulin constructs of enzymatic or recombinant origin, such as Fab, F(ab')$_2$, or ScFv.

In some embodiments, there are provided kits to facilitate the practice of any one of the methods disclosed herein.

The following terms are defined so that embodiments disclosed herein may be understood more readily. Additional definitions are set forth throughout the detailed description.

"Fatty acid" refers to an organic molecule consisting of a linear aliphatic chain terminated by a carboxyl group, with a general structural formula of $CH_3(CH_2)_nCOOH$, where n is an integer of at least one. For fatty acids suitable for practicing the present methods, "n" may be an integer of at least 4 up to 12. Specific examples of saturated fatty acids suitable for practicing methods particularly include enanthic (heptanoic, C7) acid, caprylic (octanoic, C8) acid, pelargonic (nonanoic, C9), and capric (decanoic, C10) acid. The term fatty acid may also refer to unsaturated fatty acids, containing one double bond, or a larger number of double bonds, which may occur at any position along the primary carbon chain.

"Allantoin" refers to a purine metabolite produced by oxidation of uric acid with a structural formula of $C_4H_6N_4O_3$ and an IUPAC name of 2,5-dioxo-4-imidazolidinyl urea.

"Cell culture" refers to the cultivation of cells in a liquid medium, in the present context, for the purpose of producing IgG monoclonal antibodies. Cells employed for this purpose commonly include Chinese hamster ovary (CHO) cells, but may include cell types from other mammals, as well as non-mammalian animal cells, plants, and microbes. In all cases, the liquid medium contains nutrients to support cell growth.

"Bioreactor" refers to a vessel within which cells are grown under controlled conditions. The vessel may comprise a stainless steel tank, or tank of other material, or a lined tank, or, a polymer bag of dimensions suitable to grow the number of cells required to produce a target amount of the desired antibody; equipped with sensors and inputs to permit monitoring of critical process parameters and adjustments as necessary to maintain ideal conditions for cell growth and antibody production.

"Harvest" or "cell culture harvest" generally refers to the contents of a bioreactor at termination of cell culture process. In addition to the IgG produced, the harvest will initially contain cells, cellular secretions, and expelled contents of dead cells, as well as the contents of the nutrient medium in which the cells were originally grown. These non-antibody components constitute the contaminants that are to be removed from the antibody. The particularly include host protein and DNA, but may also include virus and endotoxin. Cell culture harvests also frequently contain misassembled or damaged forms of antibodies in fragmentary forms.

"Clarified cell culture harvest" refers to a harvest from which the cells have been removed. The clarification process may amount to no more than centrifugation, or microfiltration, or a combination of the two to remove solids, or it may include the use of chemical additives or solid materials bearing chemically interactive surfaces to extract particular classes of soluble contaminants from the harvest.

"Protein" refers to any of a group of complex organic macromolecules that contain carbon; hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is grown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that are to be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. The antibodies may be produced by a single clone, in which case they are referred to as monoclonal, or from more than one clone, in which case they are referred to as polyclonal. IgG antibodies particularly refer to a class of antibodies referred to as immunoglobulin G, which may also exist as one or a mixture of subclasses, for example in humans as $IgG_1$, $IgG_2$, $IgG_3$, or $IgG_4$; or in mice as $IgG_1$, $IgG_{2A}$, $IgG_{2B}$, or $IgG_3$; or in rat as $IgG_1$, $IgG_{2A}$, $IgG_{2B}$, $IgG_{2C}$. Antibodies produced naturally or recombinantly in eukaryotic hosts may exist in a variety of glycosylated forms, while antibodies produced in non-eukaryotic hosts may exist in a variety of glycosyated and non-glycosylated forms. The term antibodies is also understood to understood to include fragmentary constructs, whether of enzymatic or proteolytic origin, including but not limited to Fab, F(ab')$_2$, VHH; and ScFv.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

A useful starting point in customizing methods disclosed herein to a particular cell culture harvest is to add dry allantoin to cell culture harvest which contains cells or has had the cells already removed, where the added allantoin amounts to 1%, w/v. Mixing is maintained throughout the addition. A portion of the allantoin dissolves but another portion remains undissolved. In water, about 0.6% dissolves and the rest remains insoluble, but in complex biological systems where the allantoin interacts with various components, the proportions may shift. Nonanoic acid is added to a proportion of 0.5%, v/v, and stirring is continued. Fatty acid addition may alternatively take place in advance of allantoin addition, or concurrent with allantoin addition, but the suggested order appears to support slightly higher recovery of antibody from the treatment. It is unnecessary in some cases to adjust pH since the negatively charged carboxyl group on the fatty acid itself reduces the pH to about 5.4. In other cases, or if a salt of the fatty acid is used, then the pH of the harvest should be adjusted to about pH 5.2. Conductivity need not be adjusted. Mixing is maintained for 2 hours, but may be reduced in subsequent experiments. Solids are optionally allowed to settle, and the liquid is clarified by any expedient method such as microfiltration or sedimentation. The clarified liquid may be optionally further treated by passage through a device with an internal liquid-contact surface populated by positive charges. No adjustment of pH or conductivity conditions is needed to add this step. The treated material may be evaluated for reduction of turbidity, host cell proteins, antibody aggregates, antibody fragments, DNA, histones, nucleosomes, virus, endotoxin, or other contaminants that may be pertinent to the goals of a particular purification.

In some embodiments, fatty acids may be introduced to the harvest in their acidic ionic form. When introduced in acidic form it may not be necessary to adjust the pH of the harvest since the fatty acid itself may titrate the working pH to a suitable value. pH may be adjusted, generally to a range of pH 4.0 to 6.0, but more ideally in a range of 4.5 to 5.5, or 4.8 to 5.2, or 5.2. More acidic conditions generally support better contaminant removal but less acidic conditions generally favor higher IgG recovery. As a general matter, the disclosed methods support good results at higher pH values than fatty acid precipitation as traditionally performed. It will be recognized that avoidance of extreme pH may reduce chemical stress imposed on the antibody and may provide secondary benefits in the form of higher recovery of functional antibody and/or improved antibody stability. Thus, it is generally beneficial to evaluate moderate pH values such as 4.5 to 5.5 as a matter of routine, despite contrary procedures commonly practiced in the art for conducting precipitation with fatty acids. Even where advance pH titration is not strictly required, it may be prudent since it may increase the reproducibility of the method. In other embodiments, fatty acids may be introduced as salts, such as sodium caprylate, or sodium pelargonate, or sodium caprate; or potassium caprylate, or pelargonate, or caprate, or other salt, such as with a potassium cation. When introduced as a salt, it will be necessary to adjust the pH of the working solution by addition of an appropriate titrating agent to achieve the desired working pH, since preparation of the salt effectively suspends the titrating capacity of the component ions. Suitable titrating agents may consist of acids or concentrated buffers pre-titrated to or near the target working pH.

Experimental data indicate that in some embodiments, capric acid is more effective than caprylic acid, especially for removal of aggregates, however, apparently due to its higher hydrophobicity, owing to its 10 atom carbon chain, it also involves higher risk of antibody losses, sometimes leading to lower recovery or erratic results from relatively minor variations in ambient temperature. Experimental findings to date indicate that the effective concentration range of capric acid is about half the concentration of caprylic acid in a similar context. This recommends 0.2% capric acid as one suitable concentration at which to begin experiments. Other experimental findings indicate that pelargonic (nonanoic acid, 9-carbon) provides a more favorable balance of hydrophobicity and charge than either caprylic or capric acid, and supports more effective host protein reduction. Other experimental results indicate that 8-nonenoic acid, a 9-carbon fatty acid with a single double bond at the terminus of the fatty acid chain, also supports better results than caprylic or capric acid.

It will generally be worthwhile to evaluate a range of values for each variable in order to determine the most effective configuration for a particular purification. Allantoin concentration may be evaluated at a lesser proportion such as 1%, or a higher proportion such as 2, 3, 4, 5%, or intermediate increments. Experimental data indicate that allantoin becomes less effective below 1%, and that antibody recovery may be compromised above 5%, but broader ranges can be evaluated so long as there is an awareness of the potential compromise that may arise. Concentrations lower than the suggested 1% may particularly compromise aggregate reduction; while higher concentrations may compromise antibody recovery. Lower antibody recovery may be acceptable in some cases due to other effects deemed to be of greater value. Experimentation with incubation conditions for addition of allantoin alone is generally not needed, since experience indicates that its effects occur very rapidly. Fatty acid concentration may be varied from 0.05% to 5%. Incubation time as little as 15 minutes will likely compromise aggregate and host protein removal but may be evaluated along with 30 minutes, or 45 minutes, or 60 minutes, or 90 minutes, or 120 minutes, or other interval of choice. Incubation times longer than 2 hours may also be evaluated but experimental data to date do not reveal a significant advantage in such intervals. Incubation time is a major determinant of efficiency but should be balanced against the economic disadvantages of long process time intervals. 16 hours is convenient as a starting point because it corresponds with overnight incubation which can be conducted unattended, but lesser intervals should also be evaluated, such as 1 hour, 2 hours, 4 hours, and perhaps lesser, greater or intermediate intervals at the discretion of the user. Operating pH for the initial incubation with the fatty acid may range from 4 to 6, or 4.5 to 5.5, or 4.8 to 5.2. Conductivity generally does not require adjustment, but can be increased to about 2 times normal physiological conductivity by addition of a salt such as sodium chloride, or reduced by about half by addition of water, or wider ranges can be evaluated if desired.

It may be desirable to evaluate nonanoic acid as an alternative to caprylic or capric acid since experimental results indicate that it is more effective in some instances for removal of antibody fragments, and generally appears to be at least as effective in all other respects. Capric acid may be considered disadvantageous when applied to cell culture harvests that are stored under refrigeration, but such concerns are suspended in situations where the fatty acid may be added directly to fresh cell culture harvest, and particularly where the cell culture harvest remains resident in the bioreactor. In the latter case, the high temperature may be maintained for any incubation interval desired. This approach may have the secondary advantage that if the temperature is reduced following the fatty acid incubation, some proportion of the capric acid will become insoluble and more likely associate with solids in the system, with the effect of increasing the efficiency of its removal from the system. Experimental data indicate that nonanoic acid may be evaluated over the same range of concentrations as caprylic acid, though it will generally be found to be effective at a lower concentration. Carbon chain lengths less than 8 are less effective, particularly with respect to aggregate removal, and consequently employ larger relative amounts, but remain potentially useful. Chain lengths of 10 carbon atoms or greater are impaired by the difficulty of achieving high concentrations of soluble reagent due to the inherent solubility of the fatty acid, and they pose a higher risk of reduced antibody recovery in some instances. As a general matter, experimental data indicate that the more hydrophobic the fatty acid, the lower its effective concentration and the narrower its dynamic range. Other organic acids combining one or more negative charges and one or more aliphatic or aromatic hydrophobic moieties, including but not limited to saturated fatty acids, unsaturated fatty acids, polyunsaturated fatty acids, and phospholipids may also be used to practice methods disclosed herein, following the guidelines suggested herein.

In some embodiments, it may be advantageous to conduct methods disclosed herein in which all of the disclosed elements are present, since the degree of influence asserted by the individual elements in the system as a whole cannot be predicted by their independent behavior. This highlights the point that the system as a whole achieves different results from conventional fatty acid treatments, through coordination with physical and chemical mechanisms that are distinct from fatty acid precipitation as practiced in the art. In practicing methods disclosed herein, single elements of the method may be serially executed to provide a streamlined approach for any particular target IgG antibody. In some embodiments, statistical techniques such as Design of Experiments (DoE), as known in the art, provide a means to identify a selection of a reduced number of method embodiments disclosed herein, designed to a particular IgG purification.

In one embodiment, the method may be applied to IgG-containing feed streams that have been processed previously by other means. In one such embodiment, a bioreactor harvest may have been treated in a manner distinct from the methods disclosed herein. It will be evident to a person of ordinary skill in the art that the presence of other chemical additives may compromise the effectiveness of the present method, or may be transparent, or that the present method may compound the beneficial effects of the previous treatment. In another such embodiment, the IgG-containing feed stream may be said to have been partially purified.

In some embodiments, the IgG to be purified may be monoclonal or polyclonal, and may reside in a biological fluid such as serum, or plasma, or other naturally-derived fluid. In such embodiments, the same method parameters may be evaluated over the same ranges as described for processing of monoclonal antibodies produced by in vitro cell culture techniques. It is to be expected that polyclonal antibodies cover a broader range of molecular behavior than a given monoclonal antibody, and that differences in behavior of antibodies derived from different species may be observed, but it will be within the purview of a person skilled in the art to adjust the elements of the methods disclosed herein without departing from the essential features of the methods as a whole.

In one embodiment, the harvest may be further processed by one or more methods after the treatment has been applied and solids removed from the system. One such embodiment may include passage of the treated harvest through a functionalized filter or other device equilibrated to the same conditions as the sample. In some such embodiments, the pH and conductivity conditions of the sample may be altered to enhance the ability of the functionalized device to extract contaminants. In another embodiment, the IgG may be concentrated and buffer exchanged by diafiltration, which will also remove some contaminants. In another embodiment, the treated harvest may be processed by high performance tangential flow filtration. In another embodiment, the clarified supernatant may be processed by cation exchange chromatography. In another embodiment, the IgG may be precipitated from the clarified harvest by polyethylene glycol. In another embodiment, IgG may be selectively precipitated from the clarified harvest by a kosmotropic salt such as ammonium sulfate, sodium sulfate, potassium phosphate, sodium citrate, or potassium citrate. In another embodiment, the clarified harvest may be processed by steric exclusion chromatography, where IgG is forced to accrete on hydrophilic particles in the presence of polyethylene glycol, or by preferential exclusion or chromatography, where the IgG is forced to accrete on particles in the presence of one or more kosmotropic salts. In another embodiment, the treated harvest may be processed by cation exchange chromatography. In another embodiment, the treated harvest may be processed by hydrophobic interaction chromatography. In another embodiment, the treated harvest may be processed by a form of so-called mixed mode chromatography, where a given chromatography medium comprises multiple chemical functionalities able to achieve different fractionation results than the constituent functionalities applied sequentially.

The following Examples are understood to be general, for illustration only, and should not be construed as limiting in any fashion.

EXAMPLES

Example 1

Contaminant removal by caprylic acid precipitation. Different amounts of caprylic acid were added to cell culture harvest clarified by centrifugation, to final concentrations of 0.1, 0.2, 0.3, 0.4, and 0.5% respectively. Allantoin was added to each sample to a final concentration of 1%. Neither pH nor salt concentration was adjusted. Final pH at 0.4% caprylic acid was 5.4. The mixtures were stirred for 2 hours. Solids were removed by passing the sample through a 0.22 µm microfilter. Host cell protein was reduced from an original 242,888 ppm of IgG in the harvest to 233,318 in 0.1% caprylic acid; 193,400 ppm in 0.2%; 57,519 ppm at 0.3%; 38,602 ppm at 0.4%; and 42,666 ppm at 0.5%. IgG fragments, including free light chain and light chain dimers were reduced from 12.2% in the harvest to 5.3% at 0.3% caprylic acid; 3.4% in 0.4%; and 3.6% in 0.5% caprylic acid. There was no fragment reduction at 0.1 and 0.2% caprylic acid. Aggregates were reduced from 1.28% in the harvest, to 1.22% in 0.1% caprylic acid, 0.87% in 0.2% caprylic acid, 0.31% in 0.3% caprylic acid, and were undetectable (less than 0.05%) at 0.4 and 0.5% caprylic acid. IgG recovery across the caprylic acid concentrations was 99% in 0.1% caprylic acid, 99% at 0.2%, 95% at 0.3%, 99% at 0.4%, and 95% at 0.5%.

Example 2

The effect of operating pH on host protein reduction. A series of experiments was run where IgG-containing microfiltration-clarified harvest was treated with 0.4% caprylic acid; pH was not adjusted in an experimental control; pH was adjusted to pH 6 and 7 in two separate experiments. Host protein content was 38,602 ppm in the unadjusted control (pH 5.4), 171,232 at pH 6.0, and 243,675 ppm at pH 7.0.

Example 3

Subsequent purification by IgG precipitation with polyethylene glycol. The samples from Example 1 treated with 0.4% and 0.5% caprylic acid, followed by the porous particle treatment, were further purified by precipitation with polyethylene glycol (PEG-6000), conducted at 20.5% PEG, 800 mM NaCl, 50 mM Hepes, pH 7.0. After PEG precipitation of harvest treated with 0.4% caprylic acid, host proteins were reduced to 11 ppm, aggregates to 0.09%, and light chain fragments were undetectable. After PEG precipitation of harvest treated at 0.5% caprylic acid, host protein was reduced to 13 ppm, aggregates to 0.1%, and light chain fragments were undetectable. These results both correspond to a 99.9995% reduction of host protein. In a parallel control experiment where the harvest was not treated by the present method, PEG precipitation reduced host protein to 67,687 ppm. The more than 6,000-fold improvement provided by the disclosed method illustrates two distinct benefits. The obvious benefit is that reduction of host protein contamination by the present method permits a follow-on method to achieve a yet greater reduction of host protein contamination. It also highlights the arguably greater benefit that the disclosed method particularly removes contaminants that interfere with the ability of the purification method itself to achieve its best results.

Example 4

Integration of the method with an anion exchange depth filter. 0.4% caprylic acid was added to cell culture harvest without any pre-treatment. Allantoin was added to a final concentration of 1%. The mixture was continuously stirred for 2 hours, then passed through a two-stage anion exchange depth filter instead of a membrane microfilter as in Examples 1-3, in preparation for the same porous particle mixture treatment described in Example 1. The depth filtration step reduced host protein 19-fold from 176,244 ppm to 9173 ppm, reduced aggregates from 2.03% to undetectable (less than 0.05%); and reduced light chain contaminants from 12% to 1%.

Example 5

Enhanced performance by protein A affinity chromatography. A sample prepared by the treatment with allantoin, caprylic acid, and mixed particles as described in Example 4 was subjected to purification by protein A affinity chromatography (ToyoPearl AF-rProtein A 650F, Tosoh Bioscience). Protein A normally reduces contaminating host protein levels to the range of 500 to 2,000 ppm of IgG when feed stream consists of cell harvest clarified by centrifugation and/or microfiltration. Performing the caprylic acid-allantoin and porous particle method described in Example 1, in advance of protein A, allowed the protein A step to achieve a host protein level below 1 ppm, and aggregates beneath the level of detectability. This particularly highlights that the disclosed method removes contaminants that interfere with the ability of protein A to fulfill its potential.

Example 6

Enhanced performance by antibody precipitation followed by anion exchange chromatography. A sample prepared by treatment with allantoin, caprylic acid and mixed particles as described in Example 4 was subjected to further purification by a mixed-mode precipitation step, initially with PEG as described in Example 3, followed by a transition to 2.0 ammonium sulfate, pH 7.0. The IgG was resolublized and tested revealing 5.9 ppm host cell protein. Aggregates were beneath the level of detection (less than 0.05%). A single follow-on polishing step of anion exchange in void exclusion mode in 50 mM Tris, pH 8.25 reduced host protein to less than 1 ppm. This result is important because it highlights the ability of the disclosed method to provide a foundation that permits inexpensive low-functioning fractionation methods to achieve better overall purification performance that processes that are based on the perceived highest performing fractionation method of all: protein A affinity chromatography.

Example 7

The disclosed method as an intermediate purification step. An experimental control was run in which cell culture harvest clarified by centrifugation and microfiltration was fractionated by precipitation as described in Example 7. This reduced host protein from 287,655 ppm to 67,687 ppm, aggregates from 2.83 to 1.57%, and antibody fragments from 10.4 to 2.3%. A follow-on anion exchange step in void exclusion mode reduced host protein 99.6% to 221 ppm and aggregates to 1.45%.

Example 8

Evaluation of different caprylic acid concentrations with and without allantoin. Cell-containing harvest was clarified by centrifugation and membrane filtration through a 0.22 micron membrane, then the pH of the supernatant was reduced to 6.0. Various subsamples were treated with caprylic acid at amounts of 0.01%, 0.05%, and 0.1%. All samples were turbid following treatment, indicating the persistence or reformation of particulates, even after precipitated materials were removed by centrifugation. The same series of experiments was repeated in the presence of 2% allantoin. Antibody recovery and reduction of contaminants was essentially equivalent but the processed material was sparkling clear after processing. This Example illustrates the contribution of allantoin to the performance of the disclosed method as a whole.

Example 9

Accelerated clarification of mammalian cell harvest by addition of allantoin. Allantoin was added to a final concentration of 1% to 5 L of cell-containing cell culture harvest containing an IgM, monoclonal antibody, among the usual spectrum of contaminants. The container was swirled gently to mix the components. Interactions between allantoin and unknown cell culture components caused this amount of allantoin to be fully dissolved, so an additional 1% was added, bringing the total added amount to 2% (w/v). The container was again swirled to mix the components. Whereas particulate materials had been observed to settle very slowly before addition of allantoin, and only slightly faster in the presence of 1% allantoin, settling rate was obviously accelerated by 2% allantoin, and left the cell culture supernatant sparkling optically clear within a period of about 20 minutes. The differential between 1% and 2% allantoin was interpreted as an indication that 1% allantoin, by virtue of the presence of some solubilizing substances in the sample, was almost completely dissolved. The supernatant was subsequently decanted. This inadvertently resuspended a portion of the precipitate, which was subsequently centrifuged to sediment the remaining solids. This highlights the ability of allantoin to improve the quality of cell harvest clarification independent of fatty acids or other additives. It also highlights the potential benefit of conducting initial trials with an allantoin concentration of at least 2%. It further highlights the important point that the solublility of allantoin may be affected by components of a sample, with the effect that a supersaturating concentration of allantoin can be determined experimentally, although its known solubility in water may provide a useful preliminary guide.

Example 10

Clarification of an *E. coli* lysate by addition of allantoin. 20 grams of *E. coli* paste in 250 mL of 50 mM Hepes, pH 7.0 past was homogenized with a microfluidizer at 16,000× g. The homogenate was then centrifuged at 15,000×g for 1 hour to remove the largest particulate species. This produced a tan-colored turbid supernatant. Dry allantoin was added directly to the supernatant to a final concentration of 5% w/v. The mixture was swirled for about 1 minute than allowed to settle. Insoluble materials settled within a few minutes leaving a sparking clear supernatant that contained more than 90% of the protein product that was present in the original homogenate. The supernatant passed easily through a 0.22 micron membrane filter, where supernatant prior to allantoin treatment clogged the filter virtually on contact. This Example highlights the ability of allantoin to dramatically improve the filterability of a treated sample, and highlights the independent contribution of allantoin to the performance of the method as a whole. It also illustrates that the disclosed method is not restricted to antibodies grown by mammalian cell culture.

Example 11

Recovery of antibody and endotoxin reduction from an IgG-endotoxin mixture using allantoin. Endotoxin was added to 1 mg/mL human IgG in 5 mM HEPES 100 mM NaCl pH 7.0 to 22,000 EU/ml. 2% (w/v) allantoin was added to aliquots of this mixture and allowed to mix for 15 minutes at room temperature. The suspension was clarified by centrifugation. Protein and endotoxin concentrations were measured to calculate antibody recovery and endotoxin removal. 2% (w/v) allantoin reduced endotoxin twofold. Antibody recovery was unaffected by the amount of allantoin. In a subsequent series of experiments, the amount of allantoin was increased in increments, up to 10%. Antibody recovery diminished gradually to about 93% at 10% allantoin, while endotoxin removal efficiency increased to about 99%. These experiments illustrate that the use of larger amounts of allantoin can result in a loss of IgG. Additional experiments with proteins ranging in size from about 12 kDa to 1 MDa indicated a definite trend whereby the loss of protein increases with increasing protein size. This Example illustrates the ability of allantoin to enhance the performance of the disclosed method as a whole.

Example 12

A viral culture containing $10^{10}$ particles per mL of minute virus of mice was coreciptitated under physiological conditions by addition of allantoin in an amount of 10%. Infectivity testing of the supernatant documented removal of 99.9% of the virus. Another viral culture containing $10^{10}$ particles per mL of murine leukemia virus was co-precipitated under physiological conditions by addition of allantoin in an amount of 10%. Infectivity testing of the supernatant documented removal of 99.9% of the virus. This Example illustrates the independent contribution of allantoin to the disclosed method as a whole.

Example 13

Non-interactivity of DNA and fatty acids. Caprylic acid precipitation has been described as having the ability to precipitate DNA (Brodsky et al supra). This does not make sense because their identical negative charges should repel each other. This was confirmed in an experiment in which purified DNA at concentrations of 1 2, 5, an 10 micrograms per mL was combined with 0.4% caprylic acid at pH 5.2 and physiological conductivity for 2 hours. No significant differences were observed in the DNA concentrations after treatment. This shows that apparent DNA binding described by others is attributable to indirect binding through an intermediate species, which according to research by Gan et al (supra), is likely the histone Example 14

Contaminant reduction by caprylic acid precipitation. Experiments were run to document a baseline for clarification performance by caprylic acid. All experiments were conducted on an IgG-containing cell culture harvest containing 259,777 ppm host protein and aggregates amounting to about 30% of the non-aggregated IgG. All experiments were conducted at physiological conductivity. Effects on host protein, IgG recovery, and aggregate content were evaluated at 0.5 pH unit intervals from 3.5 to 7.0. Highest host protein reduction was at pH 3.5, but IgG recovery was less than 50%. Highest aggregate removal was at pH 4.5. Highest IgG recovery was at pH 6.5 and 7.0, but host protein and aggregate reduction were poor. Results are given in the table below.

| pH  | Host proteins (ppm) | IgG recovery (%) | Aggregate (%) |
|-----|---------------------|------------------|---------------|
| CCH | 260k                | 100              | 23.7          |
| 3.5 | 56.6k               | 46               | 7.9           |
| 4.0 | 78.3k               | 43               | 3.2           |
| 5.5 | 90.4k               | 76               | 2.9           |
| 5.0 | 102k                | 83               | 4.1           |
| 5.5 | 115k                | 89               | 5.1           |
| 6.0 | 257k                | 94               | 15.8          |
| 6.5 | 246k                | 100              | 16.6          |
| 7.0 | 266k                | 105              | 16.6          |

Example 15

The combined influence of pH and conductivity in the absence of the functionalized particle addition. A series of experiments was conducted, evaluating the effects of pH 4.8, 5.2, and 5.6, each at conductivity values of 12 mS/cm, 16 mS/cm, and 20 mS/cm. The starting material was a. cell culture harvest containing the same antibody, plus 213,821 ppm host protein, and 25.6% aggregates. The data show that the disclosed method, even limited to the allantoin and caprylic acid components, achieves substantially better results than caprylic acid alone (Example 30). Complete results are described in the following table.

| pH/cond. | Host proteins (ppm) | IgG recovery (%) | Aggregate (%) | FLC (%) |
|---|---|---|---|---|
| CCH | 195k | 100 | 22.9 | 23.6 |
| 4.8 | | | | |
| 12 | 4556 | 79 | 1.0 | 0.4 |
| 16 | 5977 | 89 | 3.0 | 0.3 |
| 20 | 7433 | 89 | 3.0 | 0.7 |
| 5.2 | | | | |
| 12 | 2237 | 92 | 0.9 | 0.2 |
| 16 | 4340 | 100 | 1.8 | 0.9 |
| 20 | 4937 | 101 | 0.9 | 0.8 |
| 5.6 | | | | |
| 12 | 9679 | 100 | 0.8 | 14.5 |
| 16 | 35k | 100 | 0.8 | 17.0 |
| 20 | 44k | 100 | 0.9 | 14.1 |

Example 16

The influence of solid and dissolved calcium compounds on the disclosed method. An IgG-containing cell culture harvest also containing 652,450 ppm and 34.1% aggregates was treated with 1% allantoin, 0.4% caprylic acid, various concentration of calcium chloride or hydroxyapatite, titrated to pH 5.2 and mixed for two hours. Solids were removed and the samples evaluated. Calcium concentrations ranging from 0.5 to 8.0 mM had no significant effect on IgG recovery. HCP was in the range of ~70,000-80,000 ppm, light chain content was barely reduced, and aggregate levels were generally reduced to ~2.5%. Hydroxyapatite at v:v concentrations of 0.5 to 4% reduced IgG recovery from 79% at 0.5% HA to 38% at 8% HA. Host protein was reduced but the reductions were less than the loss of IgG. Light chain content was not reduced effectively. Aggregates were reduced to the lowest values in the study, but not sufficiently to compensate for antibody losses. Data are presented in the following table. CAspecies refers calcium chloride. (CC) or hydroxyapatite (HA) respectively. The line labeled "Base" indicates results obtained without any calcium additives.

| CAspecies | Host proteins (ppm) | IgG recovery (%) | Aggregate (%) | FLC (%) |
|---|---|---|---|---|
| CCH | 652k | 100 | 34.1 | 26.3 |
| Base | 73k | 86 | 2.4 | 23.2 |
| CA | | | | |
| 0.5 mM | 75k | 87 | 4.1 | 24.3 |
| 1 mM | 73k | 86 | 2.6 | 27.8 |
| 2 mM | 71k | 87 | 2.3 | 28.3 |
| 4 mM | 82k | 83 | 2.2 | 25.5 |
| 8 mM | 70k | 83 | 2.6 | 25.1 |
| HA | | | | |
| 0.5% | 58k | 80 | 1.5 | 30.6 |
| 1% | 23k | 75 | 0.8 | 23.8 |
| 2% | 9k | 67 | 1.4 | 24.6 |
| 4% | not detected | 55 | 1.8 | 34.9 |
| 8% | not detected | 38 | 0.2 | 26.8 |

Example 17

The effect of nonionic surfactants. 1% allantoin was added to each of 4 50 mL aliquots of cell culture harvest clarified by centrifugation and microfiltration. One was retained as a control. Tween-20 was added to the other three in amounts of 0.005, 0.01, and 0.02% respectively. The samples were incubated for 10 minutes followed by addition of caprylic acid to 0.4%, and adjustment to pH 5.3 by addition of 1 M acetic acid, then incubation for 2 hours. Samples were removed and filtered for analysis. TREN particles (BioWorks, Workbeads TREN, high) were added to the remainder of the sample in an amount of 5%, mixed for 4 hours, then the solids removed by microfiltration. Up to the point of adding TREN particles, aggregate content was reduced from the control to 0.005% Tween, then again at 0.01% Tween, but did not improve further with 0.02% Tween. Antibody recovery and content of excess free light chain were roughly unchanged. After TREN particle addition, aggregate level was the same across all samples, and light chain content was little-affected, but IgG recovery increased with Tween content up to 0.01% though not further at 0.02%.

| OM | Host proteins (ppm) | IgG recovery (%) | Aggregate (%) | FLC (%) |
|---|---|---|---|---|
| CCH | 416k | 100 | 20.3 | 33.4 |
| Before TREN Tween-20 | | | | |
| 0.000% | 137k | 91 | 20.8 | 26.7 |
| 0.005% | 132k | 89 | 16.8 | 25.2 |
| 0.01% | 160k | 90 | 5.9 | 25.7 |
| 0.02% | 151k | 89 | 7.5 | 26.6 |
| After TREN Tween-20 | | | | |
| 0.000% | 6109 | 78 | 1.7 | 0.4 |
| 0.005% | 5627 | 81 | 1.7 | 0.1 |
| 0.01% | 6247 | 88 | 1.7 | 0.4 |
| 0.02% | 8039 | 87 | 1.8 | 2.1 |

Example 18

The effects of nonionic, zwitterionic, and cationic surfactants. 1% allantoin was added to each of 50 mL aliquots of cell culture harvest clarified by centrifugation and microfiltration. One was retained as a control. The following surfactants were added to each of two aliquots at 0.01% and 0.05% respectively: Glycholic acid ethoxylate 4-nonylphenl ether (Glych., nonionic), Ethylenediamine propoxylate-block-ethoxylate tetrol (TET, nonionic), Brij 58 (Pluronic F-127, nonionic), Triton X-100 (nonionic), Nonidet P40 (nonionic), 3-[(3-cholamidopropyl)dimethylammonio]-1-propanesulfonate hydrate (CHAPS, zwitterionic), Hexadecyltrimethylammonium bromid (CTAB, cationic), Dodecyltrimethylammonium bromide (DDTAB, cationic), decyltrimethylammonium bromide (DTAB) cationic), myristyltrimethylammonium bromide (MTAB, cationic), octadecyltrimethylammonium bromide (OTAB, cationic). The samples were incubated for 10 minutes followed by addition of caprylic acid to 0.4%, and adjustment to pH 5.3 by addition of 1 M acetic acid, then incubation for 2 hours.

| OM | Host proteins (ppm) | IgG recovery (%) | Aggregate (%) | FLC (%) |
|---|---|---|---|---|
| CCH | 394k | 100 | 13.3 | 26.2 |
| CaprAll. | 3928 | 86 | 1.7 | 1.5 |
| Glych.01% | 4209 | 81 | 1.4 | 1.8 |

-continued

| OM | Host proteins (ppm) | IgG recovery (%) | Aggregate (%) | FLC (%) |
|---|---|---|---|---|
| Glych.05% | 5655 | 83 | 2.1 | 5.1 |
| F127.01% | 55k | 84 | 1.5 | 1.8 |
| F127.05% | 76k | 85 | 1.8 | 0.5 |
| TET.01% | 5204 | 87 | 1.7 | 6.6 |
| TET.05% | 3138 | 88 | 1.3 | 2.0 |
| Brij.01% | 11k | 87 | 3.5 | 6.5 |
| Brij.05% | 26k | 93 | 1.9 | 1.6 |
| Triton.01% | 7241 | 90 | 1.9 | 1.6 |
| Triton.05% | 16k | 92 | 3.9 | 11.5 |
| Ndet.01% | 7519 | 91 | 1.6 | 1.2 |
| Ndet.05% | 16k | 92 | 3.8 | 10.5 |
| CHAPS.01% | 6884 | 85 | 1.2 | 1.9 |
| CHAPS.05% | 8700 | 89 | 1.8 | 3.3 |
| CTAB.01% | 2278 | 86 | 1.1 | 1.3 |
| CTAB.05% | 23k | 86 | 10.3 | 1.7 |
| DDTAB.01% | 5274 | 90 | 1.2 | 2.0 |
| DDTAB.05% | 76k | 91 | 1.8 | 4.4 |
| DTAB.01% | 7281 | 88 | 1.5 | 23.7 |
| DTAB.05% | 42k | 91 | 1.8 | 13.6 |
| MTAB.01% | 9405 | 89 | 1.3 | 4.9 |
| MTAB.05% | 98k | 90 | 1.7 | 16.9 |
| OTAB.01% | 6155 | 89 | 1.1 | 7.0 |
| OTAB.05% | 53k | 89 | 1.4 | 15.4 |

Example 19

The effects of different fatty acids. 1% allantoin was added to each of 50 mL aliquots of cell culture harvest clarified by centrifugation and microfiltration. One was retained as a control. Caprylic acid to 0.4% was added as another control, and pH adjusted to 5.3 by addition of 1 M acetic acid, then incubated mixing for 2 hours. 5 Aliquots of harvest were treated with 0.1%, 0.2%, 0.3%, 0.4%, and 0.5% 2-ethylhexanoic acid (EHA). These experiments were repeated with 3-heptenoic acid (3HA), then with 3-octenoic acid (3OA), and 8-nonenoic acid (8NA).

| Samp. | Host proteins (ppm) | IgG recovery (%) | Aggregate (%) | FLC (%) |
|---|---|---|---|---|
| CCH | 400k | 100 | 13.8 | 31.4 |
| Capry.4% | 14k | 92 | 1.4 | 5.5 |
| EHA.1% | 226k | 89 | 2.0 | 20.8 |
| EHA.2% | 180k | 92 | 2.0 | 20.7 |
| EHA.3% | 154k | 98 | 1.7 | 20.4 |
| EHA.4% | 214k | 89 | 1.7 | 20.9 |
| EHA.5% | 188k | 87 | 1.7 | 20.2 |
| 3HA.1% | 123k | 79 | 1.9 | 22.1 |
| 3HA.2% | 130k | 78 | 1.7 | 21.3 |
| 3HA.3% | 135k | 79 | 1.6 | 21.1 |
| 3HA.4% | 113k | 76 | 1.5 | 20.2 |
| 3HA.5% | 116k | 75 | 1.6 | 20.2 |
| 3OA.1% | 123k | 79 | 1.9 | 21.9 |
| 3OA.2% | 108k | 78 | 1.6 | 21.6 |
| 3OA.3% | 107k | 78 | 1.6 | 19.7 |
| 3OA.4% | 84k | 74 | 1.3 | 13.3 |
| 3OA.5% | 23k | 69 | 1.3 | 6.7 |
| 8NA.1% | 160k | 70 | 2.0 | 26.9 |
| 8NA.2% | 160k | 85 | — | 25.7 |
| 8NA.3% | 123 | 83 | 1.7 | 19.3 |
| 8NA.4% | 9735 | 85 | 1.5 | 4.9 |
| 8NA.5% | 1600 | 83 | 1.4 | 2.6 |

Example 20

Comparison of octanoic acid and 8-heptenoic acid, with and without functionalized particles. 1% allantoin was added to each of 50 mL aliquots of cell culture harvest clarified by centrifugation and microfiltration. One was retained as a control. Caprylic acid to 0.4% was added as another control, and pH adjusted to 5.3 by addition of 1 M acetic acid. The mixture incubated mixing for 2 hours and a sample was removed for testing, then TREN particles were added in an amount of 5% (v:v), and incubated mixing for an additional 4 hours. Solids were removed by microfiltration then analysed. This experimental format was repeated with 8-heptenoic acid at 0.4%, 0.5%, and 0.6%.

| Samp. | Host proteins (ppm) | IgG recovery (%) | Aggregate (%) | FLC (%) |
|---|---|---|---|---|
| CCH | 416k | 100 | 20.3 | 33.4 |
| Before TREN | | | | |
| Capry.4% | 137k | 91 | 20.8 | 26.7 |
| 8NA.4% | 147k | 91 | 18.6 | 26.6 |
| 8NA.5% | 124k | 90 | — | 22.1 |
| 8NA.6% | 71k | 89 | 14.0 | 21.8 |
| After TREN | | | | |
| Capry.4% | 6108 | 78 | 17 | 0.4 |
| 8NA.4% | 4353 | 91 | 1.8 | 1.7 |
| 8NA.5% | 4561 | 78 | 1.5 | nd |
| 8NA.6% | 6225 | 59 | 0.9 | nd |

As illustrated by the examples, the disclosed methods may be combined with other purification methods to achieve higher levels of purification. Examples of such other purification methods include but are not limited to other methods commonly used for purification of IgG, such as protein A and other forms of affinity chromatography, anion exchange chromatography, cation exchange chromatography, hydrophobic interaction chromatography, and mixed mode chromatography methods; also methods of precipitation, including antibody precipitation with nonionic polymers such as polyethylene glycol or antibody precipitation with salts such as ammonium sulfate, sodium sulfate, potassium phosphate, sodium citrate, or potassium citrate; also methods of crystallization and two-phase aqueous extraction. It is within the purview of a person of ordinary skill in the art to develop appropriate conditions for the various methods and integrate them with the methods disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present embodiments.

Many modifications and variations of the embodiments disclosed herein can be made without departing from their spirit and scope, as will be apparent to those skilled in the art. The specific embodiments described herein are offered by way of example only and are not meant to be limiting in any way. It is intended that the specification and examples be considered as exemplary only, with the true scope and spirit of the embodiments disclosed herein being indicated by the following claims.

What is claimed is:

1. A method of purifying an antibody comprising:
   (a) contacting a cell culture harvest or a protein preparation comprising at least one antibody with at least one fatty acid having 7 to 10 carbon atoms to form a mixture;
   (b) contacting the mixture with allantoin; and
   (c) removing solid materials from the IgG-containing liquid.

2. The method of claim 1, wherein the allantoin is present at a concentration in a range selected from the group consisting of: (a) from about 0.6 to about 30%, (b) from about 1 to about 10%, and (c) from about 1 to about 2%.

3. The method of claim 1, wherein allantoin is in a range from a non-zero amount up to about 0.6%.

4. The method of claim 1, wherein the solid materials are removed by sedimentation, centrifugation or combinations thereof.

5. The method of claim 1, wherein the solid materials are removed by filtration.

6. The method of claim 5, wherein the filtration comprises membrane filtration or depth filtration.

7. The method of claim 6, wherein the membrane filtration or depth filtration comprises a contact surface that is functionalized.

8. The method of claim 1, wherein the cell culture harvest or protein preparation contains cells, and optionally resides in a bioreactor in which cell culture production was performed.

9. The method of claim 1, wherein the cell culture harvest or protein preparation does not contain cells.

10. The method of claim 1, wherein the protein preparation is a naturally occurring biological fluid.

11. The method of claim 1, wherein the at least one fatty acid comprises a general structural formula of $CH_3(CH_2)_n COOH$, wherein n is an integer from 5 to 8.

12. The method of claim 1, wherein the at least one fatty acid comprises enanthic (heptanoic) acid, caprylic (octanoic) acid, pelargonic (nonanoic) acid, or capric (decanoic) acid.

13. The method of claim 1, wherein the at least one fatty acid contains at least one double bond.

14. The method of claim 13, wherein the at least one fatty acid comprises nonenoic acid.

15. The method of claim 13, wherein the at least one fatty acid comprises nonenoic acid with the double bond at the terminal position.

16. The method of claim 1, wherein the at least one fatty acid is present at a concentration in a range selected from the group consisting of: (a) from about 0.05 to about 5%, (b) from about 0.1 to about 1.0%, (c) from about 0.2 to about 0.4%, and (d) from about 0.1 to 0.2%.

17. The method of claim 1, wherein the mixture further comprises a surfactant.

18. The method of claim 17, wherein the surfactant is nonionic, or zwitterionic, or cationic.

19. The method of claim 18, wherein the cationic surfactant is cetyltrimethylammonium bromide.

20. The method of claim 19, wherein the cetyltrimethylammonium bromide is present at a concentration ranging from about 0.001% to 0.05%, or from about 0.005% to 0.025%, or from about 0.0075% to about 0.01%.

* * * * *